United States Patent [19]

Hach et al.

[11] Patent Number: 4,865,992

[45] Date of Patent: Sep. 12, 1989

[54] SYSTEM AND METHOD FOR QUANTITATIVE ANALYSIS OF A SOLUTION

[75] Inventors: Clifford C. Hach; John G. Wasson, both of Loveland, Colo.

[73] Assignee: Hach Company, Loveland, Colo.

[21] Appl. No.: 901,321

[22] Filed: Aug. 28, 1986

[51] Int. Cl.⁴ .............................................. G01N 35/00
[52] U.S. Cl. ............................................ 436/51; 422/75; 422/76; 422/81; 436/43; 436/163; 436/164
[58] Field of Search ................ 422/75, 76, 81, 82; 436/43, 51, 52, 53, 163, 164, 166; 138/40, 44

[56] References Cited

U.S. PATENT DOCUMENTS

| | | | |
|---|---|---|---|
| 1,498,682 | 6/1924 | Dailey | 138/44 |
| 2,992,077 | 7/1961 | Schneider, Jr. et al. | 422/81 |
| 3,019,091 | 1/1962 | Schneider, Jr. | 422/67 |
| 3,769,178 | 10/1973 | Rothermel, Jr. | 436/163 |
| 4,199,323 | 4/1980 | Miller, Jr. et al. | 436/163 |
| 4,231,990 | 11/1980 | Jottier | 422/81 |

*Primary Examiner*—Barry S. Richman
*Assistant Examiner*—Timothy M. McMahon
*Attorney, Agent, or Firm*—Dean P. Edmundson

[57] ABSTRACT

A system and method for quantitative analysis of a solution to determine the concentration of a chemical species in the solution. The system includes a reaction vessel; a source of at least one liquid reagent for reacting with the chemical species being tested for; a conduit leading from the reagent source to the reaction vessel; pneumatic pressure for forcing the reagent through the conduit; controls for controlling the amount of reagent added to the reaction vessel; and a detection device for detecting reaction between the reagent and the chemical species.

22 Claims, 1 Drawing Sheet

SYSTEM AND METHOD FOR QUANTITATIVE ANALYSIS OF A SOLUTION

FIELD OF THE INVENTION

This invention relates to analysis of chemical compositions. More particularly, this invention relates to analysis of liquid compositions. Even more particularly, this invention relates to systems and techniques for quantitatively determining the concentration of a chemical species in a solution.

BACKGROUND OF THE INVENTION

Analysis of a liquid composition to determine the presence and concentration of a particular chemical species is well-known. There are various techniques which have previously been used for this purpose, e.g., colorimetric analysis, titration to a particular pH, voltage (potentiometric titration), conductivity (amperometric titration), etc.

One or more of such techniques may be useful in analysis of a liquid composition containing an unknown concentration of a particular chemical species which is reactive with a reagent to produce a product which is different in at least one measurable physical property from (a) the particular chemical species in question, and (b) the reagent being used. For example, the resulting product may differ in terms of color, electrical potential, pH, conductivity, etc. By observing the occurrence of the reaction product it is possible to determine the amount of the particular chemical species which was present in the original sample.

The manner in which these processes have been carried out previously involves the addition of a single known amount of reagent to a solution containing a given amount, or concentration, of the chemical species to be determined, and then observing for the occurrence of the reaction product. For example, the occurrence of the reaction product may be noted by a color change, or pH change, conductivity change, etc.

An alternative method utilizes the incremental addition of reagent to a reaction vessel containing the chemical species in a manner such that the chemical species is consumed and a sudden property change is observed due to the complete absence of the free chemical species.

This incremental addition method is well known as titration. Known amounts of reagent are added to the solution to consume the chemical species in question. When the particular chemical species is completely consumed (i.e. no free chemical species remaining), a sudden and complete change in some physical property is noted. Then the concentration of the chemical species is calculated as a function of the amount of reagent added to produce the change (or endpoint) rather than as a function of the magnitude of the change after the addition of a uniform amount of reagent.

The property which changes to signify the endpoint may be color (colorimetric titration), pH, voltage (potentiometric titration), conductivity (amperometric titration), etc.

The addition of reagent to the solution in the previously known procedures referred to above may be performed manually, if desired. More recently there have been proposed devices which automatically inject reagent into a reaction vessel in which the solution to be tested is contained. Such devices are commercially available and involve a syringe filled with the desired reagent to be used. A piston in the syringe is caused to move by means of a controlled stepper motor to force reagent out of the syringe.

The controlled stepper motor can rotate in precise increments, and such rotation is translated (via a screw mechanism) to a linear motion which drives a piston in a syringe. The motor can actuate in both directions and thus can fill as well as dispense, although a diverting mechanism must be used so that the syringe can fill from one vessel and dispense into a separate (reaction) vessel. The piston in the syringe requires seals at the piston head. Such seals can develop leaks with passage of time (due to cold-flowing of the seal to release tension) and with continued use (due to scarring of the seal or the barrel wall by particulates).

There has not heretofore been provided systems or apparatus for automatic analysis of solutions having the advantages of the present invention.

SUMMARY OF THE PRESENT INVENTION

In accordance with the present invention there is provided a system for quantitative analysis of a solution to determine the concentration of a particular chemical species in the solution. In one embodiment the system comprises:

(a) a reaction vessel;

(b) addition means for adding the test solution to the reaction vessel;

(c) a source of liquid reagent which is adapted to react with the particular chemical species in the solution;

(d) conduit means communicating between the reagent and the reaction vessel;

(e) pneumatic pressure means adapted to force the reagent through the conduit means to the reaction vessel;

(f) control means adapted to control the amount of reagent added to the reaction vessel; and (g) detection means adapted to detect the reaction between the reagent and the chemical species in the reaction vessel.

The system of this invention does not require or involve the use of pistons and syringes, nor does it require the use of stepper motors. Also, the source of liquid reagent(s) may be of any size, and any desired number or types of reagents may be used in this system. Accordingly, the system is readily adaptable for use in on-line process work.

Furthermore, the system and techniques of the invention are adaptable to a wide variety of chemical analyses, e.g., colorimetric analysis and titrations or volumetric reactions such as potentiometric (e.g., pH), amperometric and specific ion electrode titrations. The system is also useful in analyses where a certain observable phenomenon takes place, which may be for example a change in magnitude of some physical characteristic. Also, multiple analyses of different types can be performed in sequence.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
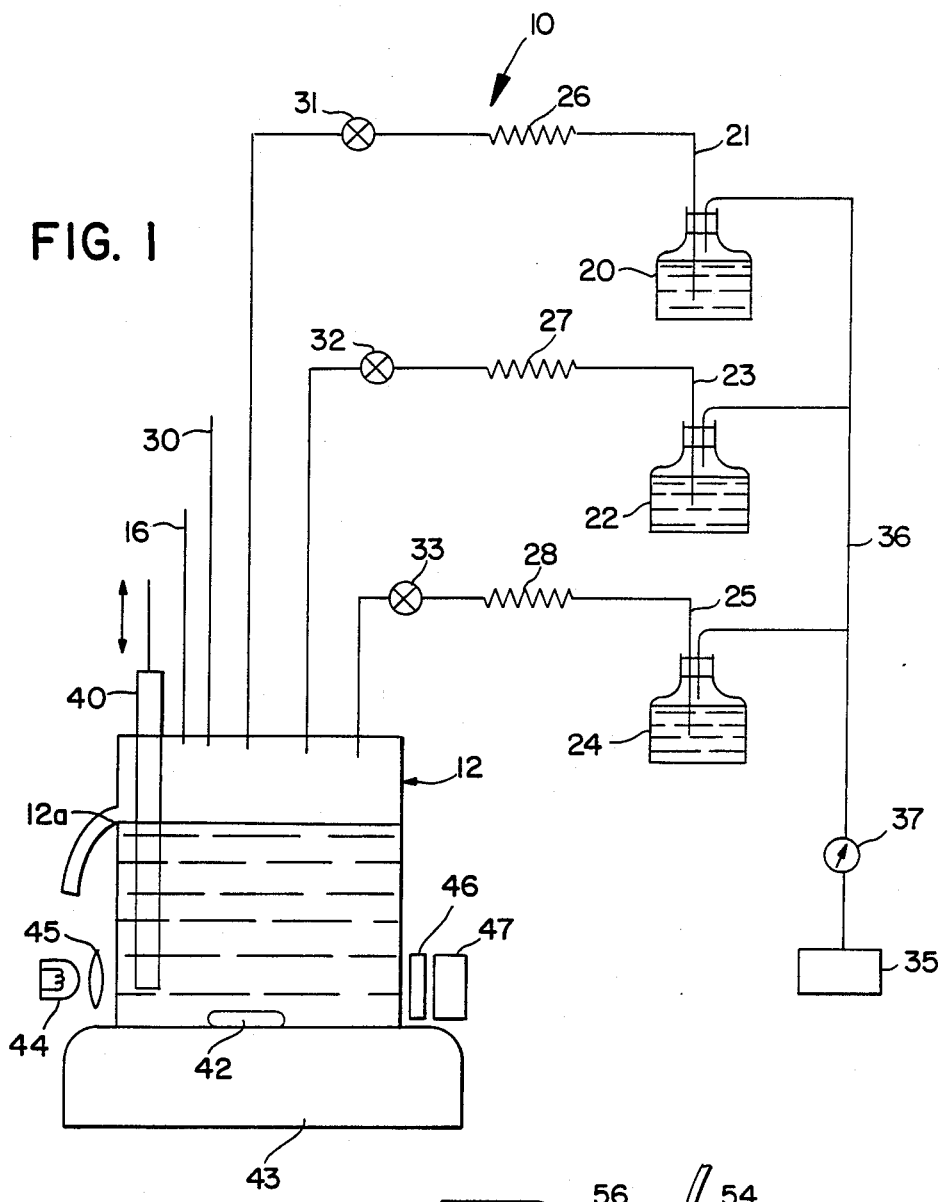
FIG. 1 is a schematic illustration of one embodiment of the invention.

In FIG. 1 there is illustrated one embodiment of a pressure driven analysis system 10 of the invention. In this embodiment there is a reaction vessel 12 and a plurality of liquid reagent sources 20, 22 and 24.

The system illustrated in FIG. 1 is useful for quantitative analysis of a solution to determine the concentration of a particular chemical species in the solution. A sample inlet line 30 is adapted to feed the solution to be tested into the reaction vessel 12. Reagent feed lines (i.e., conduits) 21, 23 and 25 extend from the reagent sources to the reaction vessel, as illustrated. Preferably the exit end of each feed line or conduit touches an interior wall of the reaction vessel so that no drops of reagent remain suspended at the end of the feed line. Flow restrictors 26, 27 and 28 are present in the feed lines. Valves 31, 32 and 33 are also present in the feed lines.

Each reagent source is operably connected to a source of pressure 35 by means of line 36. Valve 37 in line 36 controls the extent of the pressure in line 36. Each reagent container includes a stopper at the top thereof through which the pressure line and the feed line extend, as illustrated. Preferably the pressure in line 36 is in the range of about 4 to 30 psi. The pneumatic source may be compressed gas or liquid such as carbon dioxide (gas) or Freon (liquid).

Preferred flow restrictors are composed of fused silica capillary tubing having an internal diameter of 250 micrometers. The flow of fluid through such tubing is proportional to driving pressure and inversely proportional to the length of the tubing. The tubing is inert with respect to the reagents. Flow is also a function of fluid viscosity which, in turn, is affected by temperature. Therefore, it is preferable to maintain the temperature of the restrictors constant. It is also possible to not thermostat the flow restrictors and simply note the ambient temperature and adjust the calculations accordingly.

Other types of flow restrictors may also be used, if desired. For example, a tiny orifice could be used. A matrix of sintered material pressed together could also be used. A needle valve could also be used if it were inert to the reagents and sufficiently precise and accurate in operation.

The valve in each reagent feed line is preferable a pinch valve (when the feed line is a flexible tubing) or a Teflon poppet valve. The valve preferably has an actuation time of one second or less and must act in a repeatable fashion. Flow rate of reagent through a valve can be accomplished by modulating the valve pulse frequency.

The valve may be controlled by means of a solenoid which pulses the valve open and then closed. Each time the solenoid pulses the valve open a small amount of reagent is forced through the valve. The length of the flow restrictor, the driving pressure, and the time during which the valve is open govern the volume of reagent passing through the valve on each pulse. For example, in a system having a driving pressure of 6 psi, a valve pulse of one second, and a flow restrictor one meter long (250 micrometers in internal diameter), a volume of six microliters of reagent will pass through the valve in one pulse.

Preferably there is a movable bob 40 or other type of displacement means associated with the reaction vessel. The bob which is illustrated in FIG. 1 is an elongated cylindrical member which is adapted to be raised or lowered. When the sample solution is being introduced into the reaction vessel the bob is in its lowered position. After the sample solution has filled the reaction vessel and has started to flow over the weir 12a and out the exit tube, no further sample solution is added. Then the bob 40 may be raised (either partially or completely) so as to lower the level of the sample solution in the vessel 12 below the weir. Then when the reagents are added to the reaction vessel no sample solution or reagent is lost over the weir during the analysis. In FIG. 1 the bob is shown in its lower most position. Feed line 16 is adapted to feed into the reaction vessel an appropriate cleaning agent for the reaction vessel.

A magnetic stirrer 42 powered by motor 43 is used to assure proper and uniform mixing of the contents of the reaction vessel while the various reagents are added. When the analysis is to be a colorimetric analysis, for example, a light beam from lamp 44 is collimated by lens 45 and then shone through the reaction vessel and also through filter 46 before being received by photodetector 47.

When it is desired to add reagents to the sample solution in the reaction vessel it is only necessary to open the valve corresponding to the desired reagent feed line or conduit. For example, when it is desired to add reagent 20 to reaction vessel 12, it is only necessary to open valve 31. Pressure from line 36 then forces reagent 20 through line 21, flow restrictor 26, and valve 31 so that it will be introduced into reaction vessel 12. Similarly, when adding other reagents to the reaction vessel, the same procedure is followed.

In this embodiment, any or all of the reagents may be added simultaneously, if desired, since each reagent feed line contains its own valve. Although FIG. 1 illustrates the use of three separate reagent sources, there may be any number of reagent sources used. After all required reagents have been added, the colorimetric analysis may be conducted.

In the case of a unit volume colorimetric analysis the necessary reagents, buffers, etc. are dispensed as a single volume. The reaction vessel is the cell of a colorimeter. After a few moments of delay, the signal from the colorimeter is digitized and the necessary calculations are performed. The result may be displayed (e.g., on a display panel) and charted or transmitted digitally to a remote computer.

In volumetric analyses the buffers and indicators, if required, are dispensed as unit volumes into the reaction vessel as soon as the solution sample has been added to the vessel. Then a small volume of titrant is added to the sample. The titrant reacts with the particular chemical species being tested for in the sample. After a short delay, the output from the detection means (e.g., pH meter, colorimeter, etc.) is digitized, and that value is stored along with a record of the corresponding volume of titrant added. The process is repeated (with successive amounts of titrant being added) until an endpoint is reached, which is indicated by a dramatic shift in detector signal with the addition of the equivalence of the titrant. Calculations are then performed to find the concentration of the particular chemical species in the solution being tested. The amount of the chemical species in the sample is a direct function of the amount of titrant required in order to reach the endpoint.

The volume of the reaction vessel may vary, although it should have a volume of at least one milliliter and may be as large as 400 milliliters. A preferred and convenient size is 22 milliliters. The exact volume of the reaction vessel is not critical so long as the system is calibrated with the same volume of standard solution as is used for the size of the solution sample to be tested.

Other types of displacement means may also be used. For example, an inflatable submerged balloon may be located in the reaction vessel. The balloon can be inflated before the sample solution is added and then deflated so as to provide sufficient room for the reagents to be added. Another type of displacement means is a movable wall or floor in the reaction vessel which can be moved after the sample solution is added to provide additional space in the reaction vessel.

As an alternative, the reaction vessel may be filled to a predetermined volume with sample solution to be tested, which volume is less than the total volume of the vessel. Then the necessary reagents may be added without exceeding the total volume of the vessel.

As a further alternative, a reaction vessel having a weir as shown in FIG. 1 may be used. The sample solution may be added until it reaches the weir, then the weir may be closed or covered (e.g., with a door). Then the required reagent solutions may be added for analysis of the solution sample.

Figure 2:
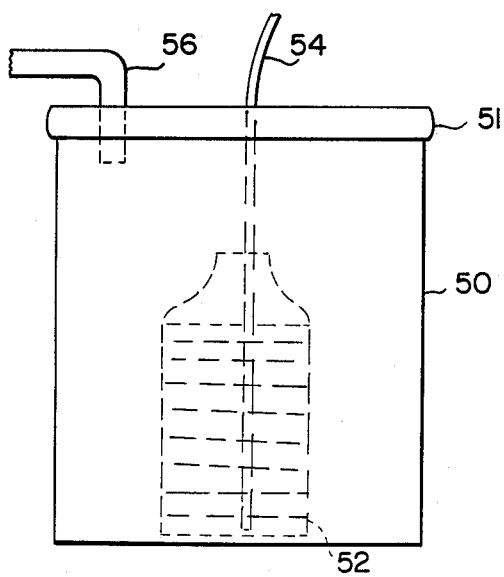
FIG. 2 illustrates another manner of pneumatically forcing reagent through conduit means in accordance with the invention.

In FIG. 2 there is illustrated another manner of forcing liquid reagent from a source container 52 through conduit means 54 to a reaction vessel. The container is placed inside of an explosion-proof container 50 having cover 51 threadably secured thereto. Conduit means 54 extends through the cover 51 and into the reagent container 52. Pressure line 56 extends through cover 51, as illustrated, and pressurizes the container 50 to the desired pressure (e.g., 4 to 30 psi). If desired, a floating pickup may be used on the end of the conduit means in the reagent container. In this manner the end of the conduit floats at the surface of the reagent in the container.

The system of the invention is useful for a wide variety of quantitative chemical analyses of solutions (aqueous, organic, blends, etc.). Examples of specific analyses for which the system of the invention is especially useful include: water hardness, chromate ion in water, silica in water, water alkalinity, free chlorine and total chlorine in water, acid-base titrations, and ammonia in water.

Various types of detection means may be employed. For example, the detection may be colorimetric, where radiation (visible or near infrared) is imprinded on a photoelectric detector. The absorbance of light due to the presence of a particular chemical species is proportional to the concentration of that species in the test solution.

The detection may also be potentiometric, where two inert electrodes in the system measure the oxidation and reduction potentials at the cathode and anode, respectively. The net potential is a function of the concentration of the particular chemical species being tested for in the test solution.

The detection may also be pH, which is a type of potentiometric determination. A glass electrode is used which is permeable to hydrogen ions. A potential is developed and measured.

The detection may also be by way of conductivity, for example. A potential is applied across two electrodes which are immersed in the test solution. The potential is usually developed using A.C. The resulting current is measured and is proportional to the concentration of the conducting species being tested for in the solution.

The instrument is calibrated by analyzing a sample with a known concentration of the chemical species to be determined in subsequently tested samples. The analysis is performed and, in the case of a unit volume analysis, the magnitude of property change is noted.

In a volumetric analysis the amount of reagent required to reach the equivalence point is noted. From this data a response factor can be calculated. By means of the response factor, subsequent analyses are ratioed against the response of the known concentration to calculate the concentration of the unknown in the test solution. The calibration is performed using a standard solution.

The reaction vessel is cleaned chemically. A cleaning solution such as a strong acid (e.g., sulfuric acid) or a strong base (e.g., sodium hydroxide) may be introduced into the reaction vessel instead of test solution. After a period of time sufficient to clean the reaction vessel, the cleaning solution is replaced by the test solution.

The invention is further illustrated by means of the following examples:

EXAMPLE 1

City water was tested for silica content using colorimetric analysis and the apparatus illustrated in FIG. 1, except that only two reagent sources were required and no bob was required. The reaction vessel had a capacity of 22 milliliters.

The water to be tested was forced through a feed line, controlled by a solenoid valve, to the reaction vessel until the vessel was filled to the weir. Then 0.1 ml. of Molybdate 3 reagent solution (commercially available from Hach Company) and 0.1 ml. of citric acid were added by forcing them pneumatically from their respective reagent sources through the feed lines to the reaction vessel.

After a 30 second incubation period the test solution is analyzed colorimetrically (at 460 nm.) in the reaction vessel. This analysis revealed that the silica content of the water was 1.8 parts per billion. Satisfactory repeatability was demonstrated with successive samples.

EXAMPLE 2

A standard solution containing 0.8 parts per million nitrogen (using urea as a nitrogen source) was tested using the apparatus and system of FIG. 1 except that no bob was required. The reaction vessel was filled with the test solution and then Nessler's reagent was added, and 0.1 ml. of polyvinyl alcohol was also added. After an incubation period of one minute the solution is tested colorimetrically.

The reaction between the reagent and the nitrogen in the reaction vessel will produce a film on the glass cell (i.e., reaction vessel) which will interfere with the optical clarity of the vessel unless the film is removed after each analysis. Consequently, repetitive analyses were conducted as a test of the ability to clean or remove this film from the glass surface. After each colorimetric analysis 0.1 ml. of sulfuric acid was added to the reaction vessel to clean the glass surface. Thirty-two repetitive analyses were then conducted over a period of 5.5 hours with consistently accurate results in colorimetric analysis of the test solution, thus demonstrating the effectiveness of the clean-up procedure.

EXAMPLE 3

Various samples of water solutions were prepared with different, known concentrations of magnesium sulfate. The water solutions were tested by colorimetric titration using the apparatus of FIG. 1. After the reaction vessel was filled with each test solution, the bob was raised. It was determined that the bob displaced a volume of 1.5 ml. (approximately the expected volume of reagents to be added to the test solution during the analysis).

Then 0.25 ml. of buffer solution (magnesium EDTA) and 0.1 Calmagite-TEA indicator were added to the test solution. The test solution was then titrated with 0.20 M $Na_3HEDTA$. Initially, injections of the titrant are made every three seconds. Colorimetric analysis (at 460 nm.) is conducted continuously, with the results displayed on a continuous chart. The slope of the graph produced on the chart is constantly appraised, and when the slope begins to increase quickly the titration process is slowed to one injection every six seconds. The concentration of the magnesium ion is proportional to the amount of titrant used. The titration process produced consistently accurate results.

EXAMPLE 4

City water was tested for alkalinity (i.e., bicarbonate concentration) using the apparatus of FIG. 1 except that a pH meter was used to detect the endpoint of the reaction. This is a form of potentiometric titration.

The water sample in the reaction vessel was titrated with 0.02N sulfuric acid, and 6 microliters of the titrant were added every 5 seconds until the test solution exhibited a pH of 5.3. Then the titrant was injected every 30 seconds. When the test solution exhibited a pH of 4.8 the endpoint of the titration is reached. The alkalinity of the test solution is proportional to the amount of titrant used. Consistently accurate results are observed.

The system and techniques of this invention are extremely versatile and efficient. The amount of desired reagent(s) to be added to the reaction vessel can be very precisely controlled by opening the appropriate valve for each reagent feed line for a predetermined period of time. No pumps or other such equipment is required in order to move reagent through the feed lines.

What is claimed is:

1. A system for quantitative analysis of a solution to determine the concentration of a chemical species present in said solution, said system comprising:
   (a) a single reaction vessel;
   (b) addition means for adding said solution to said reaction vessel;
   (c) a source of liquid reagent, said reagent being capable of reacting with said chemical species in said solution;
   (d) conduit means communicating between said source of liquid reagent and said reaction vessel; wherein said conduit means includes a feed line which extends into said source of liquid reagent;
   (e) pneumatic pressure means comprising a source of gas at a pressure in the range of about 4 to 30 p.s.i. for applying a constant positive pneumatic pressure to said liquid reagent to force said reagent into said feed line and through said conduit means to said reaction vessel;
   (f) control means adapted to control the amount of said reagent added to said reaction vessel; and
   (g) detection means adapted to detect reaction between said reagent and said chemical species in said reaction vessel.

2. A system in accordance with claim 1, wherein said reaction vessel has a predetermined volume.

3. A system in accordance with claim 1, further comprising additional sources of additional reagents.

4. A system in accordance with claim 1, further comprising displacement means adapted to displace a predetermined volume of said reaction vessel, said displacement means being movable between first and second positions.

5. A system in accordance with claim 1, wherein said detection means comprises a light source and a photodetector, wherein said photodetector is adapted to detect light transmitted from said light source through said reaction vessel.

6. A system in accordance with claim 1, wherein said detection means comprises a pH meter.

7. A system in accordance with claim 1, wherein said detection means comprises a potentiometer.

8. A system in accordance with claim 1, wherein said control means comprises:
   (a) valve means in said conduit means; and
   (b) flow restrictor means in said conduit means.

9. A system in accordance with claim 8, wherein said flow restrictor means comprises an elongated tube having a smaller diameter than said conduit means.

10. A system for quantitative analysis of a solution to determine the concentration of a chemical species present in said solution, said system comprising:
    (a) a single reaction vessel of predetermined volume;
    (b) addition means for adding said solution to said reaction vessel;
    (c) a source of liquid reagent, said reagent being capable of reacting with said chemical species in said solution;
    (d) conduit means communicating between said source of liquid reagent and said reaction vessel; wherein said conduit means includes a feed line which extends into said source of liquid reagent;
    (e) pneumatic pressure means comprising a source of gas at a pressure in the range of about 4 to 30 p.s.i. for applying a constant positive pneumatic pressure to said liquid reagent to force said reagent into said feed line and through said conduit means to said reaction vessel;
    (f) control means adapted to control the amount of said reagent means added to said reaction vessel; said control means including valve means; and
    (g) detection means adapted to detect reaction between said reagent and said chemical species in said reaction vessel.

11. A system in accordance with claim 10, wherein said liquid reagent means comprises a plurality of separate reagent solutions.

12. A system in accordance with claim 10, wherein said control means further comprises flow restrictor means in said conduit means.

13. A system in accordance with claim 10, wherein further comprising displacement means adapted to displace a predetermined fraction of the volume of said reaction vessel, said displacement means being movable between first and second positions.

14. A system in accordance with claim 10, wherein said detection means comprises a light source and a photodetector, wherein said photodetector is adapted to detect light transmitted from said light source through said reaction vessel.

15. A system in accordance with claim 10, wherein said detection means comprises a pH meter.

16. A system in accordance with claim 10, wherein said detection means comprises a potentiometer.

17. A method for quantitatively determining the concentration of a chemical species in a solution, said method comprising the steps of:
 (a) adding a predetermined volume of said solution to a reaction vessel;
 (b) providing a source of reagent which is capable of reacting with said chemical species in said solution;
 (c) providing conduit means which communicates between said source of liquid reagent and said reaction vessel; wherein said conduit means includes a feed line which extends into said source of liquid reagent;
 (d) forcing said reagent through said conduit means to said reaction vessel by means of pneumatic pressure comprising a source of gas at a pressure in the range of about 4 to 30 p.s.i. which applies a constant positive pneumatic pressure to said liquid reagent to force said reagent into said feed line and through said conduit means;
 (e) controlling the amount of said liquid reagent added to said reaction vessel; and
 (f) detecting the reaction between said reagent and said chemical species.

18. A method in accordance with claim 17, wherein a plurality of reagents are provided, wherein separate conduit means communicate between each said reagent and said reaction vessel, and wherein each said reagent is forced through a respective conduit means to said reaction vessel by means of pneumatic pressure.

19. A method in accordance with claim 17, wherein said reaction is detected colorimetrically.

20. A method in accordance with claim 17, wherein said reaction is detected by means of a pH meter.

21. A method in accordance with claim 17, wherein said reaction is detected by means of a potentiometer.

22. A method in accordance with claim 17, wherein said reaction is detected by means of a conductivity meter.

* * * * *